United States Patent [19]

Kwass

[11] Patent Number: 5,393,518
[45] Date of Patent: Feb. 28, 1995

[54] CLEAR ROLL-ON ANTIPERSPIRANT COMPOSITION

[75] Inventor: Jill A. Kwass, Andover, Mass.

[73] Assignee: The Gillette Company, Boston, Mass.

[21] Appl. No.: 997,149

[22] Filed: Dec. 24, 1992

Related U.S. Application Data

[63] Continuation of Ser. No. 618,704, Nov. 27, 1990, abandoned, which is a continuation-in-part of Ser. No. 447,622, Dec. 8, 1989, abandoned.

[51] Int. Cl.$^6$ .......................... A61K 7/32; A61K 7/34; A61K 7/38; A61K 9/10
[52] U.S. Cl. .......................... 424/66; 424/68; 514/938
[58] Field of Search .................. 424/68, 66

[56] References Cited

U.S. PATENT DOCUMENTS

| | | | |
|---|---|---|---|
| 3,957,969 | 5/1976 | Fujiyama | 424/68 |
| 4,120,948 | 10/1978 | Shelton | 424/68 |
| 4,122,029 | 10/1978 | Gee | 424/68 |
| 4,265,878 | 5/1981 | Keil | 424/68 |
| 4,268,499 | 5/1981 | Keil | 424/68 |
| 4,383,988 | 5/1983 | Tong | 424/68 |
| 4,673,570 | 6/1987 | Soldati | 424/68 |
| 4,708,863 | 11/1987 | Bews | 234/68 |
| 4,725,431 | 2/1988 | Hourihan | 424/68 |
| 4,782,095 | 11/1988 | Gum | 424/68 |
| 4,801,447 | 1/1989 | Gum | 424/68 |
| 5,162,378 | 11/1992 | Guthauser | 514/785 |

FOREIGN PATENT DOCUMENTS

| | | | |
|---|---|---|---|
| 291334 | 11/1988 | European Pat. Off. | 424/68 |
| 404532 | 12/1990 | European Pat. Off. | 424/66 |

OTHER PUBLICATIONS

Dow Corning, "Information About Cosmetic Ingredients" (1984).
"Deodorant & Antiperspirant Formulary", *Cosmetics and Toiletries*, vol. 100, pp. 65–75 (Dec. 1985).

Primary Examiner—Dale R. Ore
Attorney, Agent, or Firm—Stephan P. Williams

[57] ABSTRACT

An optically clear liquid antiperspirant product in the form of a stable water-in-oil emulsion with a viscosity of less than about 1000 cps at about room temperature includes an aqueous phase with an antiperspirant active ingredient in solution therein, an oil phase making up at least about thirty percent of the product, and a stabilizing agent that has a substantial solubility in each of the oil and aqueous phases. The emulsion has long term stability over temperature ranges from about 0° to 45° C. The product preferably is dispensed as a thin film from a roll-on type dispenser.

6 Claims, No Drawings

CLEAR ROLL-ON ANTIPERSPIRANT COMPOSITION

This application is a continuation of application Ser. No. 07/618,704, filed Nov. 27, 1990, now abandoned, which is a continuation-in-part of application Ser. No. 07/447,622, filed Dec. 8, 1989, now abandoned.

This invention relates to antiperspirant products and processes for forming antiperspirant products.

Antiperspirant products are well-known in the cosmetic art and typical antiperspirants contain an active antiperspirant ingredient and a vehicle. The active antiperspirant ingredient acts to reduce perspiration, it is believed, by interacting in solution with sweat glands. Antiperspirant products may be in the form of a dispersion, solution or suspension, e.g., a solid suspension such as a stick or a solid-liquid suspension such as an aerosol or a roll-on. The product may also be an emulsion, which is a stable, homogeneous mixture of immiscible liquids such as an aqueous phase and an oil phase. Antiperspirant emulsion products may have a range of viscosities from a free standing gel that is used by rubbing an area of the body such as the underarm to a liquid form emulsion that may be applied as a roll-on to apply a layer to the skin. It is desirable that all antiperspirant products have aesthetic characteristics of smoothness, non-oiliness and non-tackiness. Another desirable characteristic is that no readily visible residue as, e.g., a white layer, be on the skin after an antiperspirant is applied. It is also important that the product efficiently introduce the antiperspirant active ingredient to the sweat glands.

In accordance with one aspect of the invention, there is provided an efficacious liquid antiperspirant product that is clear, washable, leaves no visually perceptible residue, and dries quickly. The product, unlike a gel which typically includes a colloidal suspension in a coagulated condition, is a stable, free-flowing liquid water-in-oil emulsion with a viscosity of less than about 1000 cps at about room temperature. The emulsion includes an aqueous phase with an antiperspirant active ingredient in solution therein, an oil phase making up at least about thirty percent of the product and a stabilizing agent. The stabilizing agent has a substantial solubility in the aqueous and oil phases and stabilizes the emulsion in the temperature range from about 0° to 45° C. without impairing the room temperature clarity of the product. The product produces a thin film when applied to the skin and has a use range from about room to body temperature. The product preferably has a viscosity of about 500–900 cps at room temperature and may be dispensed from a roll-on type dispenser. Percentages given herein are in weight percent.

An optically clear antiperspirant product of the invention is one that is visually clear, with a minimal amount of haziness or cloudiness. Like glass, the product allows ready viewing of objects behind it. By contrast, a translucent antiperspirant product, although allowing light to pass through, causes the light to be so scattered that it will be impossible to see clearly objects behind the translucent product. Preferably, the product has a refractive index (measured at 5893Å) of 1.39–1.42 at 21° C., and an optical clarity better than one hundred NTU (Nephelometric Turbidity Units) at 21° C. and is packaged in a container of the roll-on type that has an optically clear wall. The turbidity measurements discussed hereinafter were made with a Orbeco-Hellige #965 Direct-Reading Turbidimeter.

Preferably the product is stable for at least a period of three months. A stable emulsion, as discussed herein, is one that does not phase-separate into distinct oil and water portions over time and under normal temperature conditions of use. The stabilizing agent is a bridging component that has a significant solubility in the aqueous phase, and enhances stability of the emulsion at low viscosities suitable for roll-on application. Additionally, the stabilizing agent does not impair the clarity of the product. The stabilizing agent preferably includes a polyalkoxylated alcohol and a lower alcohol such as ethanol, methanol or propanol that solubilizes the polyalkoxylated alcohol, the lower alcohol having a molecular weight less than the polyalkoxylated alcohol. The polyalkoxylated alcohol also improves the washability of the product since the oil phase of the emulsion is generally insoluble in water. Particular polyalkoxylated alcohols are Oleth-5 and PPG-10 Butanediol. Preferably the stabilizing agent is soluble at five percent or more in the oil and water phases.

The oil phase preferably makes up more than about thirty percent of the product and includes an emulsifier which when properly mixed with the polar components yields a water-in-oil emulsion. The oil phase preferably comprises one or a combination of polyether substituted water-in-oil silicone emulsifiers such as cyclomethicone and dimethicone copolyol, dimethicone, and cyclomethicone. Volatile silicones, for example, cyclomethicones such as D-4, DC 244 or DC 344 may be used to enhance the dryness of application. Other silicones such as dimethicones, for example, DC-200, may be employed as a detackifier. (All above available from Dow Corning). A particular emulsifier is a polyether substituted silicone such as cyclomethicone and dimethicone copolyol (available as DC 3225C from Dow Corning).

The aqueous phase includes one or a combination of polar species such as water and propylene glycol and an antiperspirant active ingredient in solution. Preferred active antiperspirant components for use in the antiperspirant products include well-known salts of aluminum chloride, aluminum zirconium chlorohydrates, polyhydroxy complexes of basic aluminum salts, and such salts buffered, for example, with glycine or a polyglycol. Propylene glycol may be added for emolliency and for refractive index adjustment. A multipurpose adjunct, such as ethanol, may also be added for refractive index modification, aesthetic properties and antimicrobial activity.

Products of the invention also provide essentially complete absence of discernible whitening, and high antiperspirant activity. The liquid product, a substantially clear emulsion with a significant proportion of water, has reduced whitening effect as the antiperspirant active is maintained in solution. At the same time, the dissolved antiperspirant ingredient can interact with the sweat glands for effective sweat reduction.

A particular antiperspirant product has an oil phase of about 28 to 30% volatile silicone, about 8 to 10% silicone emulsifier and about 1 to 2% nonvolatile silicone; an aqueous phase of about 25 to 40% water, about 3 to 5% propylene glycol and about 15 to 20% antiperspirant active; and a stabilizing agent that includes about 0.5 to 1.5% polyalkoxylated alcohol and about 4 to 15% lower alcohol.

Preferably, the refractive indices of the aqueous and oil phases are substantially matched and the refractive index of the product is between about 1.39 to 1.42. The product can also contain additional ancillary ingredients such as emollients, colorants, fragrances, and preservatives such as antioxidants. When the stabilizing agent includes Oleth-5, it is preferred to use an antioxidant such as Tocopherol (e.g. Covi-Ox T-70 (Henkel)) in an amount of about 0.2% of the amount of Oleth-5.

Products of the invention are made by preparing an emulsion with a viscosity of less than about 1000 cps at room temperature. From an aqueous phase including an antiperspirant active in solution therein, an oil phase and a stabilizing agent having at least five percent solubility in the aqueous phase. The aqueous phase, the oil phase, and the stabilizing agent are mixed such that the oil phase makes up at least thirty percent of the product and the mixture is processed to produce a stable emulsion with a viscosity of less than about 1000 cps at room temperature (21° C). Preferably, a fragrance is solubilized in the stabilizing phase and then combined with the aqueous phase. The mixture of the stabilizing phase and the aqueous phase is then added to the oil phase as the oil phase is being sheared in an in-line device to form a stable emulsion of viscosity of under 1000 cps at room temperature.

The following Examples 1–4 are given by way of illustration only and are not to be considered as being limiting. Example 5 is outside the scope of the invention and is included for comparison purposes. The amounts in the Examples and the claims are in weight percent.

In each of the following Examples, about thirty kilograms of product is made. The ingredients of the oil phase, the aqueous phase and the stabilizing agent are formulated. The combined stabilizing phase and aqueous phase are then added to the oil phase at room temperature and are sheared in a continuous in-line high shear device such as a Gifford-Wood tandem shear pipeline mixer or an IKA Dispax-Reactor to produce the desired emulsion with a viscosity of less than about 1000 cps at room temperature.

Example 1

| CFTA NAME | % ACTIVE |
|---|---|
| Oil Phase | |
| CYCLOMETHICONE & DIMETHICONE COPOLYOL (DC 3225C) | 8.63 |
| CYCLOMETHICONE (D-4) | 28.48 |
| DIMETHICONE (DC-200 50 cs.) | 1.72 |
| Aqueous Phase | |
| WATER | 32.50 |
| PROPYLENE GLYCOL | 4.27 |
| ALUMINUM ZIRCONIUM TETRACHLOROHYDREX-GLY | 17.50 |
| Stabilizing Agent | |
| OLETH-5 (EMULGIN 05) | 1.00 |
| ETHANOL (SD ALCOHOL 40, 200 PROOF) | 5.90 |
| | 100.00 |

The resulting composition of Example 1 had a viscosity of 800 cps, a measured turbidity of 31.0 NTU and remained stable for at least three months.

Example 2

| CFTA NAME | % ACTIVE |
|---|---|
| Oil Phase | |
| CYCLOMETHICONE & DIMETHICONE COPOLYOL (DC 3225C) | 8.63 |
| CYCLOMETHICONE (D-4) | 28.33 |
| DIMETHICONE (DC-200 50 cs.) | 1.72 |
| Aqueous Phase | |
| WATER | 28.23 |
| PROPYLENE GLYCOL | 4.34 |
| ALUMINUM ZIRCONIUM TETRACHLOROHYDREX-GLY | 15.20 |
| Stabilizing Agent | |
| OLETH-5 (EMULGIN 05) | 1.04 |
| ETHANOL (SD ALCOHOL 40, 200 PROOF) | 12.36 |
| FRAGRANCE | 0.15 |
| | 100.00 |

The resulting composition of Example 2 had a measured turbidity of about 25 NTU.

Example 3

| CFTA NAME | % ACTIVE |
|---|---|
| Oil Phase | |
| CYCLOMETHICONE & DIMETHICONE COPOLYOL (DC 3225C) | 8.63 |
| CYCLOMETHICONE (D-4) | 28.48 |
| DIMETHICONE (DC-200 50 cs.) | 1.72 |
| Aqueous Phase | |
| WATER | 32.50 |
| PROPYLENE GLYCOL | 4.27 |
| ALUMINUM ZIRCONIUM TETRACHLOROHYDREX-GLY | 17.50 |
| Stabilizing Agent | |
| PPG-10 BUTANEDIOL (MACOL 57) | 1.00 |
| ETHANOL (SD ALCOHOL 40, 200 PROOF) | 5.90 |
| | 100.00 |

The resulting composition of Example 3 had a viscosity of 520 cps, a refractive index of 1.3970, a measured turbidity of about 25 NTU and remained stable for at least three months.

Example 4

| CFTA NAME | % ACTIVE |
|---|---|
| Oil Phase | |
| CYCLOMETHICONE & DIMETHICONE COPOLYOL (DC 3225C) | 8.63 |
| CYCLOMETHICONE (D-4) | 28.48 |
| DIMETHICONE (DC-200 50 cs.) | 1.72 |
| Aqueous Phase | |
| WATER | 32.50 |
| PROPYLENE GLYCOL | 4.27 |
| ALUMINUM ZIRCONIUM TETRACHLOROHYDREX-GLY | 17.50 |
| Stabilizing Agent | |
| OLETH-5 (EMULGIN 05) | 0.50 |
| PPG-10 BUTANEDIOL (MACOL 57) | 0.50 |
| ETHANOL (SD ALCOHOL 40, 200 PROOF) | 5.90 |
| | 100.00 |

The resulting composition of Example 4 had a viscosity of about 800 cps, a measured turbidity of 26 NTU and remained stable for at least three months.

Example 5

| CFTA NAME | % ACTIVE |
|---|---|
| Oil Phase | |
| VOLATILE SILICONE (DC 244) | 33.00 |
| CYCLOMETHICONE-DIMETHICONE | 10.00 |

| CFTA NAME | % ACTIVE |
|---|---|
| COPOLYOL (DC 3225C) | |
| VOLATILE SILICONE (DC 200) | 2.00 |
| Aqueous Phase | |
| ALUMINUM ZIRCONIUM TETRACHLOROHYDRATE-GLY (35%) SOLN. | 50.00 |
| PROPYLENE GLYCOL | 5.00 |
| | 100.00 |

After processing, the formulation of Example 5 produced a product having a viscosity of 800 cps, and a turbidity of 11.6 NTU. However, this Example produced an unstable emulsion that separates and is therefore commercially unsuitable as an antiperspirant roll-on product.

While particular embodiments of the invention has been shown and described, various modifications will be apparent to those skilled in the art, and therefore it is not intended that the invention be limited to the disclosed embodiments or to details thereof, and departures may be made therefrom within the spirit and scope of the invention.

What is claimed is:

1. A substantially clear antiperspirant composition which is a stable water-in-oil emulsion with a viscosity less than about 1000 cps and an optical clarity better than 100 NTU at room temperature, which composition comprises by weight 28.48 percent cyclomethicone, 8.63 percent cyclomethicone and dimethicone copolyol, 1.72 percent dimethicone, 32.50 percent water, 4.27 percent propylene glycol, 17.50 percent aluminum chlorohydrate or aluminum zirconium chlorohydrate, 1.00 percent Oleth-5, PPG-10 Butanediol, or mixtures thereof, and 5.90 percent ethanol.

2. A substantially clear antiperspirant composition which is a stable water-in-oil emulsion with a viscosity less than about 1000 cps and an optical clarity better than 100 NTU at room temperature, which composition consists essentially of by weight about 28 to 30 percent volatile silicone, about 8 to 10 percent silicone emulsifier which is cyclomethicone and dimethicone copolyol, about 25 to 40 percent water with about 15 to 20 percent aluminum chlorohydrate or aluminum zirconium chlorohydrate in solution therein, about 3 to 5 percent propylene glycol, about 4 to 15 percent lower alcohol, and about 0.5 to 1.5 percent polyalkoxylated alcohol selected from the group consisting of Oleth-5, PPG-10 Butanediol and mixtures thereof.

3. The composition of claim 2 wherein the lower alcohol is ethanol.

4. The composition of claim 3 additionally comprising about 1 to 2 percent nonvolatile silicone.

5. The composition of claim 4 wherein the viscosity is about 500 to 900 cps at about room temperature.

6. The composition of claim 5 wherein the volatile silicone is cyclomethicone and the non-volatile silicone is dimethicone.

* * * * *